United States Patent [19]

Steinmann

[11] Patent Number: 4,820,829
[45] Date of Patent: Apr. 11, 1989

[54] SUBSTITUTED O-PHTHALALDEHYDES

[75] Inventor: Alfred Steinmann, Villars-sur-Glâne, Switzerland

[73] Assignee: Ciba-Geigy Corporation, Ardsley, N.Y.

[21] Appl. No.: 1,309

[22] Filed: Jan. 8, 1987

[30] Foreign Application Priority Data

Jan. 16, 1986 [CH] Switzerland .............. 146/86

[51] Int. Cl.$^4$ .................. C07F 7/02; C07F 7/22; C07F 7/30
[52] U.S. Cl. ...................... 556/87; 556/88; 556/95; 556/413; 556/416; 556/417; 556/418; 556/422; 556/436; 556/465; 556/482; 556/485
[58] Field of Search ............... 556/87, 88, 95, 413, 556/416, 417, 436, 465, 482, 485

[56] References Cited

U.S. PATENT DOCUMENTS 4,206,152 6/1980 Gosteli .............................. 568/435
4,734,481 3/1988 Steinmann ........................ 528/43

FOREIGN PATENT DOCUMENTS 0126214 11/1984 European Pat. Off. ............ 568/435

OTHER PUBLICATIONS

Chihi Aso et al., Macromolecules 2, pp. 414–419, (1969).
J. Chem. Soc., (1940), 692.
J. Org. Chem. 24, 1792, (1959).
J. Am. Chem. Soc., 81, pp. 4113–4114, (1959).
J. Am. Chem. Soc., 79, p. 6540, (1957).
J. Chem. Soc., p. 3640, (1959).
J. Organometallic Chem., 84, pp. 165–175, (1975).
Organic Syntheses, 34, pp. 82–85, (1954).
Bulletin de la Soc. Chin. de France, 9, pp. 2966–2971, (1966).
J. Am. Chem. Soc., pp. 6540–6542, 79, (1957).

Primary Examiner—Mary C. Lee
Assistant Examiner—Zinna Northington
Attorney, Agent, or Firm—Harry Falber

[57] ABSTRACT

There are disclosed novel substituted o-phthalaldehydes of formula I

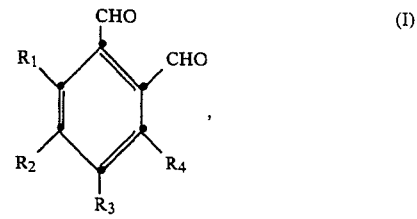

wherein at least one of the substituents $R_1$, $R_2$, $R_3$, $R_4$ is Q(alkyl)$_3$, —CH$_2$—Q(alkyl)$_3$, —O—Q(alkyl)$_3$, —Q(aryl)$_3$ or —Q(alkylenearyl)$_3$, wherein Q is Si, Sn or Ge, the alkyl moieties contain 1 to 12 carbon atoms, the aryl groups contain 6 or 12 ring carbon atoms and the alkylene radicals contain 1 to 4 carbon atoms, and each of the remaining substituents $R_1$ to $R_4$ is a hydrogen or halogen atom or a cyano, nitro, carboxyl or hydroxyl group, a C$_1$–C$_4$alkoxy, C$_1$–C$_4$alkylthio or an alkoxycarbonyl group containing 1 to 4 carbon atoms in the alkoxy moiety.

The novel o-phthalaldehydes can be polymerized to give polymers that can be used as photoresists.

10 Claims, No Drawings

SUBSTITUTED O-PHTHALALDEHYDES

The present invention relates to substituted o-phthalaldehydes, to the preparation thereof, and to the novel di- and tetrachloro or di- and tetraiodo compounds employed for the synthesis thereof.

In "Macromolecules", 1969, 2, pp. 414–419, it is taught that o-phthalaldehydes can be polymerised in the presence of specific catalysts. In EP patent application No. 0 126 214 it is further disclosed that polymers of phthalaldehydes can be used as photoresists, although 10% by weight of onium salts have to be added to the resists for them to be sufficiently radiation-sensitive at an energy of 2-6 mJ/cm$^2$. Moreover, these polymers are not stable in oxygen plasma.

It has now been found that o-phthalaldehydes that contain at least one substituent on the basis of specific silyl, stannyl or germanyl groups, can also be polymerised to give polymers that have a comparably greater sensitivity to radiation if less onium salt is added and the energy density is lower. In addition, these polymers are very stable in oxygen plasma.

Accordingly, the present invention relates to substituted o-phthalaldehydes of formula I

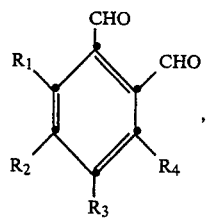
(I)

wherein at least one of the substituents $R_1$, $R_2$, $R_3$ and $R_4$ is Q(alkyl)$_3$, —CH$_2$—Q(alkyl)$_3$, —O—Q(alkyl)$_3$, —Q(aryl)$_3$ or —Q(alkylenearyl)$_3$, wherein Q is Si, Sn or Ge, the alkyl moieties contain 1 to 12 carbon atoms, the aryl groups contain 6 or 12 ring carbon atoms and the alkylene radicals contain 1 to 4 carbon atoms, and each of the remaining substituents $R_1$ to $R_4$ is a hydrogen or halogen atom or a cyano, nitro, carboxyl or hydroxyl group, a C$_1$-C$_4$alkoxy, C$_1$-C$_4$alkylthio or an alkoxycarbonyl group containing 1 to 4 carbon atoms in the alkoxy moiety.

In formula I, one or two of $R_1$, $R_2$, $R_3$ and $R_4$ are each preferably a tri(C$_1$-C$_4$alkyl)silyl, tri(C$_1$-C$_4$alkyl)stannyl or a tri(C$_1$-C$_4$alkyl)-germanyl group and each of the other substituents $R_1$ to $R_4$ is a hydrogen atom.

In particular, $R_2$ and $R_3$ in formula I are a tri(C$_1$-C$_4$alkyl)silyl radical and each of the other substituents $R_1$ to $R_4$ is a hydrogen atom.

Particularly preferred and interesting compounds of formula I are those wherein $R_2$ or $R_3$ are a trimethylsilyl or triethylsilyl group and each of the other substituents $R_1$ to $R_4$ is a hydrogen atom.

The aryl moieties contained in the substituents $R_1$ to $R_4$ may carry one or more substituents. Suitable substituents are halogen atoms, preferably chlorine or bromine atoms or nitro groups. Examples of suitable aryl groups are phenyl, chlorophenyl, naphthyl and chloronaphthyl.

Suitable alkylene groups in $R_1$ to $R_4$ are for example methylene or ethylene.

The substituted o-phthalaldehydes of formula I can be prepared either by oxidising a substituted dihalo compound of formula II

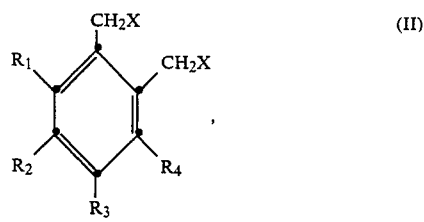
(II)

wherein each X independently of the other is a bromine, chlorine or iodine atom and $R_1$, $R_2$, $R_3$ and $R_4$ are as defined for formula I, to the corresponding compound of formula I, in known manner, with at least the equivalent amount of hexamethylenetetramine or dimethylsulfoxide; or, preferably, hydrolysing a substituted tetrahalo compound of formula III

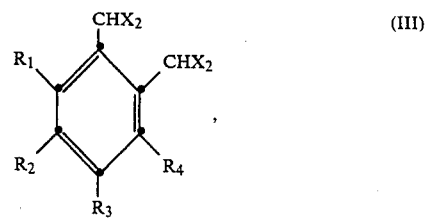
(III)

wherein each X is independently of the other a bromine, chlorine or iodine atom and $R_1$, $R_2$, $R_3$ and $R_4$ are as defined for formula I, in known manner, with a metal or ammonium salt of an organic acid in aqueous medium, and in the presence of a phase transfer catalyst and an inorganic base, or by reacting said compound of formula III with at least the equivalent amount of calcium carbonate in water or of potassium oxalate in ethanol, or with the 8-fold molar amount of morpholine, and subsequently hydrolysing the substituted di-(N-morpholino)-1,3-phthalan obtained as intermediate to a compound of formula I, or reacting said intermediate with a 0.5- to 15-fold amount of formic acid, at elevated temperature, to give a compound of formula I.

To prepare the compounds of formula I it is preferred to use a substituted tetrabromo compound of formula III and to hydrolyse said compound with a metal or ammonium salt of an organic acid in aqueous medium in the presence of a phase transfer catalyst and an inorganic base.

The above processes for the conversion of the bromomethyl or dibromomethyl groups to aldehyde groups have already been described in the literature in respect of similar compounds. Thus in J. Chem. Soc., 1940, pp. 692–702, it is disclosed, inter alia, that the chloromethyl group can be oxidised to the aldehyde group in p-ethylbenzyl chloride with an equimolar amount of hexamethylenetetramine in an alcoholic solution, at elevated temperature and in a CO$_2$ atmosphere.

The conversion of the bromomethyl group which is substituted at the aromatic ring to the aldehyde group with dimethylsulfoxide is disclosed in J. Org. Chem., Vol. 24, 1959, pp. 1792-1993, and in J. Am. Chem. Soc., Vol. 81, 1959, pp. 4113-4114.

The conversion of a tetrahalo compound of formula III into the substituted o-phthalaldehyde of formula I by hydrolysis with a metal or ammonium salt of an organic acid, in aqueous medium and in the presence of a phase transfer catalyst and an inorganic base, can be carried out in accordance with the process disclosed in EP patent application No. 0 003 230, preferably using alkali metal salts or alkaline earth metal salts of aliphatic carboxylic acids such as formic, acetic or propionic acid as metal salts. The preferred phase transfer catalyst is preferably an onium salt, in particular a quaternary ammonium or phosphonium salt, for example a tetraalkylammonium salt or a tetraalkylphosphonium salt, preferably a corresponding halide such as tetra-n-butylammonium chloride or tetra-n-butylammonium bromide or, for example, tetra-n-butylphosphonium chloride or tetra-n-butylphosphonium bromide. Suitable inorganic bases are normally the alkali metal or alkaline earth metal bases, preferably the corresponding hydroxides, bicarbonates and, preferably, carbonates such as magnesium or calcium carbonate.

It is disclosed in J. Am. Chem. Soc., Vol. 79, 1957, pp. 6540–6542, that the dibromomethyl group which is substituted at the aromatic ring can be converted into the aldehyde group by oxidation with calcium carbonate; and the conversion of dibromomethyl groups into aldehyde groups with potassium oxalate is known from Organic Syntheses, Vol. 34, 1954, pp. 82–84.

The conversion of dibromomethyl groups which are substituted at the aromatic ring into aldehyde groups with morpholine is disclosed in Bulletin de la Soc. Chim. de France, Vol. 9, 1966, pp. 2966–2971; and DE-OS 30 21 701 teaches a process for the preparation of aromatic aldehydes by reacting corresponding benzaldehydes with formic acid at elevated temperature.

The compounds of formulae II and III, which have not yet been described in the literature, have been developed for the synthesis of the compounds of formula I and thus also fall within the scope of the present invention.

In formulae II and III, each X independently of the other is preferably a chlorine or bromine atom, one or two of $R_1$, $R_2$, $R_3$ and $R_4$ are each a tri($C_1$–$C_4$alkyl)silyl, tri($C_1$–$C_4$alkyl)stannyl or tri($C_1$–$C_4$alkyl)germanyl group and each of the other substituents $R_1$ to $R_4$ is a hydrogen atom.

Most preferably, in formulae II and III each X is a chlorine or bromine atom, $R_2$ or $R_3$ is a tri($C_1$–$C_4$alkyl)silyl radical and each of the other substituents $R_1$ to $R^4$ is a hydrogen atom.

Compounds of formula III are of particular interest, especially those wherein each X is a bromine atom, $R_2$ or $R_3$ is a trimethylsilyl or triethylsilyl group and each of the other substituents $R_1$ to $R_4$ is a hydrogen atom.

The compounds of formulae II and III can be prepared in accordance with the process described in J. Am. Chem. Soc., Vol. 79, 1957, pp. 6540–6542, by brominating compounds of formula IV,

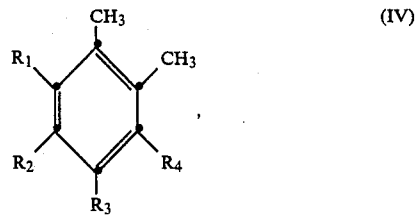

(IV)

wherein $R_1$, $R_2$, $R_3$ and $R_4$ are as defined for formula I, with N-bromosuccinamide, in the presence of a catalyst, preferably a peroxide such as dibenzoyl peroxide, to give compounds of formulae II or III.

The compounds of formula IV are known and can be prepared as described e.g. in J. Chem. Soc., 1959, page 3640, or in J. of Organometallic Chemistry, 84 (1975), 165–175, or in analogous manner.

As mentioned at the outset, the compounds of formula I are useful monomers which, when polymerised, can be used as radiation-sensitive resist material which is resistant to oxygen plasma.

EXAMPLE 1

Preparation of 4-trimethylsilyl-α,α,α',α'-tetrabromo-o-xylene

A 1.5 liter sulfonating flask equipped with cooler and stirrer is charged, under nitrogen, with 100 g (562 millimoles) of 4-trimethylsilyl-o-xylene, 400 g (2250 millimoles) of N-bromosuccinimide, 1 g of dibenzoyl peroxide and 750 ml of carbon tetrachloride. The reaction mixture is heated to boiling temperature until the reaction is exothermic. The heating bath is then removed until the spontaneous boiling subsides. Gas chromatographic analysis confirms that no more 4-trimethylsilyl-o-xylene is present. The mixture is cooled to 0° C. and the succinimide is separated. The filtrate is then extracted twice with 200 ml of cold 5% sodium hydroxide solution and washed once with water. The $CCl_4$ phase is dried over magnesium sulfate and the $CCl_4$ is expelled in a rotary evaporator.

Yield: 250 g of a solid (90% of theory) which melts at 94° C. Two recrystallisations from a small amount of n-hexane affords white crystals with a melting point of 97° C. (boiling point of the compound: 138° C./0.13 mbar).

| Elemental analysis: | theory | found |
|---|---|---|
| C [%] | 26.75 | 26.75 |
| H [%] | 2.86 | 2.87 |
| Br [%] | 64.71 | 64.54 |

$^1$H-NMR spectrum (acetone-$d_6$): $CH_3$-Si 9H (s): 0.4 ppm; $Br_2CH$ 2H (s): 7.95 ppm and 7.5 ppm; H-aromat. 3H (m): 7.6–7.85 ppm.

EXAMPLE 2

Preparation of 4,5-bis(trimethylsilyl)-α,α,α', α'-tetrabromo-o-xylene

A 1.5 liter sulfonating flask equipped with cooler and stirrer is charged, under nitrogen, with 70 g (280 millimoles) of 4,5-bis(trimethylsilyl)-o-xylene, 224 g (1260 millimoles) of N-bromosuccinimide, 5 g of dibenzoyl peroxide and 800 ml of carbon tetrachloride. The suspension is heated until the reaction is exothermic. When the exothermic reaction has subsided, the suspension is refluxed for about 3 hours and then cooled. Succinimide is removed by filtration and the filtrate is washed twice with 10% cold sodium hydroxide solution. The dried organic phase is freed from solvent and the residual solid is recrystallised from n-hexane, affording 120 g (75% of theory) of a solid which melts at 157° C.

| Elemental analysis: | theory | found |
|---|---|---|
| C [%] | 29.70 | 28.90 |
| H [%] | 3.92 | 4.02 |

| Elemental analysis: | theory | found |
|---|---|---|
| Br [%] | 56.46 | 56.38 |

$^1$H-NMR spectrum (acetone-$d_6$): CH$_3$-Si 18H (s): 0.44 ppm; Br$_2$CH 2H (s): 7.65 ppm; H-aromat. 2H (s): 8.1 ppm.

EXAMPLE 3

Preparation of 4-trimethylsilyl-o-phthaldialdehyde

A 750 ml sulfonating flask equipped with stirrer is charged with 175 g (355 millimoles) of 4-trimethyl-α,α,α',α'-tetrabromo-o-xylene, 119 g of sodium formate, 72 g of calcium carbonate, 26 g of tetrabutylammonium bromide and 150 ml of water. The mixture is heated to 100° C., under nitrogen, whereupon the 4-trimethyl-α,α,α',α'-tetrabromo-o-xylene melts.

The mixture is stirred vigorously so that the different phases are well mixed. After about 12 hours, the mixture is cooled to 0° C. and the mixture is extracted with 400 ml of diethyl ether. The dried organic phase is concentrated by evaporation. The residue is subsequently chromatographed through a column of silica gel with toluene as eluant. The toluene fractions are concentrated, affording 54 g (61% of theory) of pure 4-trimethylsilyl-o-phthaldialdehyde.

This product is dissolved in approximately the same volume of n-hexane. Yellow crystals form in the cooling cabinet. Melting point: 38° C. Boiling point of the compound: 98° C./0.13 bar.

| Elemental analysis: | theory | found |
|---|---|---|
| C [%] | 64.04 | 63.94 |
| H [%] | 6.84 | 6.96 |
| Si [%] | 13.62 | 13.04 |

$^1$H-NMR spectrum (acetone-$d_6$): CH$_3$-Si 9H (s): 0.36 ppm; H-aromat. 2H (m): 8.0 ppm; H-aromat. 1H (s): 8.1 ppm; CHO 2H (s): 10.6 ppm.

EXAMPLE 4

Preparation of 4,5-bis(trimethylsilyl)-o-phthaldialdehyde

A 750 ml sulfonating flask is charged with 85 g (150 millimoles) of 4,5-bis(trimethyl)-α,α,α',α'-tetrabromo-o-xylene, 71.5 g of sodium formate, 35 g of calcium carbonate, 113 g of tetrabutylammonium bromide, 175 ml of water and 200 ml of toluene, and the mixture is efficiently stirred at 120° C. under nitrogen. After 2 days, the reaction mixture is cooled to room temperature and diluted with toluene. The organic phase is washed with water and dried. The solvent is removed in a rotary evaporator and the solid is recrystallised from n-hexane to constant melting point. Yield: 17 g (40%) of a yellowish crystalline substance which melts at 103° C.

| Elemental analysis: | theory | found |
|---|---|---|
| C [%] | 60.38 | 59.00 |
| H [%] | 7.96 | 8.05 |

$^1$H-NMR spectrum (acetone-$d_6$): CH$_3$-Si 18H (s): 0.4 ppm; H-aromat. 2H (s): 8.3 ppm; CHO 2H (s): 10.5 ppm.

EXAMPLE 5

Polymerisation of 4-trimethylsilyl-o-phthaldialdehyde

A reactor is charged, under nitrogen, with 24 g (116 millimoles) of 4-trimethylsilyl-o-phthaldialdehyde and 100 ml of dry methylene chloride. The mixture is cooled in liquid nitrogen and 2 mol% of BF$_3$.diethyl etherate are added as initiator. The solution is then freed from oxygen under a high vacuum.

Polymerisation is carried out in a cooling bath, under nitrogen, at −78° C. After a few hours, 2 ml of a cold 1:1 mixture of −78° C. of pyridine/acetic anhydride are added to the highly viscous solution. The mixture is stirred for ½ hour at −78° C. and warmed to room temperature. The solution is poured into 1000 ml of methanol, whereupon the polymer precipitates at once. The precipitate is isolated by filtration and dried. Yield: 23.5 g. For purification, the polymer is dissolved in 300 ml of methylene chloride, the solution is filtered, and the polymer is again precipitated in 1000 ml of methanol. The precipitate is isolated by filtration and dried at room temperature under a high vacuum. Yield: 19.3 g (80% of theory).

The polymer decomposes at 156° C. Gel permeation chromatography in tetrahydrofuran gives the following values: $\overline{M}_w = 290{,}000$ and $\overline{M}_n = 80{,}000$.

EXAMPLE 6

Polymerisation of 4,5-bis(trimethylsilyl)-o-phthaldialdehyde 4 g (14.4 millimoles) of 4,5-bis(trimethylsilyl)-o-phthaldialdeyde are dissolved in an ampoule in 12 ml of dry methylene chloride. Oxygen is removed by freezing/thawing under a high vacuum. Then 2 mol%, based on the monomer, of BF$_3$.diethyl etherate solution in methylene chloride is added with a syringe to the frozen solution and polymerisation is then carried out at −78° C. under nitrogen. After a few hours, 1 ml of pyridine is added to the highly viscous solution, which has been cooled beforehand. The solution is then allowed to warm to room temperature and the polymer is precipitated from methanol. The white powder is dried, dissolved in methanol, and precipitated once more in methanol. The white polymer powder is dried under a high vacuum at 50° C., affording 3.1 g (77%) of polymer.

The polymer decomposes at 170° C. Gel permeation chromatography in tetrahydrofuran gives the following values: $\overline{M}_w = 420{,}000$ and $\overline{M}_n = 180{,}000$.

| $^1$H—NMR spectrum (CDCl$_3$): | | |
|---|---|---|
| CH$_3$—Si | 18H(s): | 0.4 ppm |
| H—aromat. | 2H(s): | 8.2 ppm |
| 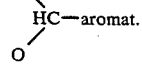 | 2H(s): | 10.6 ppm |

What is claimed is:

1. A substituted o-phthalaldehyde of formula

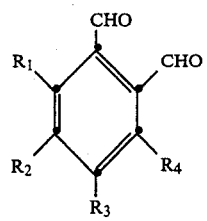

(I)

wherein at least one of the substituents $R_1$, $R_2$, $R_3$, $R_4$ is $Q(C_1-C_{12}\text{-alkyl})_3$, $-CH_2-Q(C_1-C_{12}\text{-alkyl})_3$, $-O-Q(C_1-C_{12}\text{-alkyl})_3$, $-Q(\text{aryl})_3$ or $-Q(C_1-C_4\text{-alkylene-aryl})_3$, wherein Q is Si, Sn or Ge, the aryl groups being phenyl, naphthyl or halogen- or nitro-substituted phenyl or naphthyl, and each of the remaining substituents $R_1$ and $R_4$ is a hydrogen or halogen atom or a cyano, nitro, carboxyl or hydroxyl group, a $C_1$–$C_4$alkoxy, $C_1$–$C_4$alkylthio or an alkoxycarbonyl group with 1 to 4 carbon atoms in the alkoxy moiety.

2. An o-phthalaldehyde according to claim 1, wherein one or two of $R_1$, $R_2$, $R_3$ and $R_4$ are each a tri($C_1$–$C_4$alkyl)silyl, tri($C_1$–$C_4$alkyl)stannyl or a tri($C_1$–$C_4$alkyl)germanyl group and each of the other substituents $R_1$ to $R_4$ is a hydrogen atom.

3. An o-phthalaldehyde according to claim 1, wherein $R_2$ and $R_3$ are a tri($C_1$–$C_4$alkyl)silyl radical and each of the other substituents $R_1$ to $R_4$ is a hydrogen atom.

4. An o-phthalaldehyde according to claim 1, wherein $R_2$ or $R_3$ are a trimethylsilyl or triethylsilyl group and each of the other substituents $R_1$ to $R_4$ is a hydrogen atom.

5. 4-Trimethylsilyl-o-phthalaldehyde or 4,5-bis(trimethylsilyl)—o—phthalaldehyde of formula I according to claim 1.

6. A di- or tetrahalo compound of formula II or III

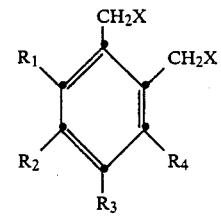

(II)

or

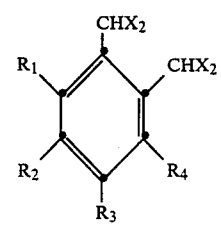

(III)

wherein each X independently of the other is a bromine, chlorine or iodine atom and at least one of the substituents $R_1$, $R_2$, $R_3$, $R_4$ is $Q(C_1-C_{12}\text{-alkyl})_3$, $-CH_2-Q(C_1-C_{12}\text{-alkyl})_3$, $-O-Q(C_1-C_{12}\text{-alkyl})_3$, $-Q(\text{aryl})_3$ or $-Q(C_1-C_4\text{-alkylene-aryl})_3$, wherein Q is Si, Sn or Ge, the aryl groups being phenyl, naphthyl or halogen- or nitro-substituted phenyl or naphthyl, and each of the remaining substituents $R_1$ to $R_4$ is a hydrogen or halogen atom or a cyano, nitro, carboxyl or hydroxyl group, a $C_1$–$C_4$alkoxy, $C_1$–$C_4$alkylthio or an alkoxycarbonyl group with 1 to 4 carbon atoms in the alkoxy moiety.

7. A di- or tetrahalo compound according to claim 6, wherein each X independently of the other is a chlorine or bromine atom, one or two of $R_1$, $R_2$, $R_3$ and $R_4$ are each a tri($C_1$–$C_4$alkyl)silyl, tri($C_1$–$C_4$alkyl)stannyl or a tri($C_1$–$C_4$alkyl)germanyl group and each of the other substituents $R_1$ to $R_4$ is a hydrogen atom.

8. A di- or tetrahalo compound according to claim 6, wherein each X is a chlorine or bromine atom, $R_2$ or $R_3$ is a tri($C_1$–$C_4$alkyl)silyl group and each of the other radicals $R_1$ to $R_4$ is a hydrogen atom.

9. A di- or tetrahalo compound according to claim 6, wherein each X is a bromine atom, $R_2$ or $R_3$ is a trimethyl or triethylsilyl group and each of the other substituents $R_1$ to $R_4$ is a hydrogen atom.

10. 4-Trimethylsilyl-$\alpha,\alpha,\alpha',\alpha'$-tetrabromo-o-xylene or 4,5-bis(trimethylsilyl)-$\alpha,\alpha,\alpha',\alpha'$-tetrabromo-o-xylene of formula III according to claim 6.

* * * * *